United States Patent [19]

Buchalter

[11] Patent Number: 4,465,074

[45] Date of Patent: Aug. 14, 1984

[54] METHOD OF APPLYING AN ELECTRODE TO THE SKIN OF A PATIENT

[76] Inventor: Gilbert Buchalter, 28 Mountainview Rd., Millburn, N.J. 07041

[21] Appl. No.: 370,278

[22] Filed: Apr. 20, 1982

[51] Int. Cl.$^3$ ............................................. A61B 5/04
[52] U.S. Cl. ................................. 128/639; 128/803
[58] Field of Search ............... 128/639, 640, 641, 803, 128/802

[56] References Cited

U.S. PATENT DOCUMENTS 3,027,333  3/1962  Friedman .................... 128/639 X
3,954,100  5/1976  Sem-Jecobsen ................ 128/639
4,416,274 11/1983  Jacobsen et al. ............. 128/803 X

FOREIGN PATENT DOCUMENTS 816466  3/1981  U.S.S.R. ..................... 128/639

Primary Examiner—Lee S. Cohen
Attorney, Agent, or Firm—Lerner, David, Littenberg, Krumholz & Mentlik

[57] ABSTRACT

A method is disclosed for applying electrode to the skin of a patient in which a thin film of a conductive liquid is applied to the skin of the patient. The thin film is of sufficient thinness so that electrical signals will be conducted through the thickness direction of the film to or from an electrode attached to the skin but so that there will be substantially no conductance of the electrical signals along the surface direction of the film to or from adjacent areas surrounding the electrode. The electrode is then applied to the skin of the patient via the thin film. Electrical signals can be detected from the patient or transmitted to the patient via the electrode and conductive thin film, e.g., ECG signals.

15 Claims, No Drawings

METHOD OF APPLYING AN ELECTRODE TO THE SKIN OF A PATIENT

BACKGROUND OF THE INVENTION

The present invention relates to a method for attaching an electrode to the skin of a patient and conducting of electrical signals to or from the skin of the patient through a thin film of a conductive liquid.

Conductive gels, creams, pads and paste have previously been used as contact media for applying electrodes to the skin of a patient. Gels, creams, pads and pastes have, however, had certain disadvantages in their use. Specifically, gels, creams, pads and pastes many times gave inaccurate readings because it is hard to control application of the gels, creams, or pastes so that adjacent electrodes do not interfere with one another because of the conductance through the gels, creams, or pastes, i.e., the electrodes were shorted out because of overlap of the gel or paste sites. Thus, the person applying the gel or paste had to be careful to avoid connection between adjacent areas where the electrodes were to be applied.

In addition, gels and pastes are messy and require specific clean-up steps after their use. Moreover, certain gels, creams, and pastes can stain the clothing of the patient.

Thus, it would be highly advantageous to avoid these disadvantages of gels, creams, pads, and pastes, while providing an easy to use and economical contact medium for electrodes.

SUMMARY OF THE INVENTION

It has now been found that s very convenient, economical, accurate and clean method for applying electrodes to the skin of a patient can be provided by applying a thin film of a conductive liquid to the skin of the patient wherein the thin film is of sufficient thinness so that electrical signals will be conducted through the thickness direction of the film to an electrode attached to the skin through said film, but so that there will be substantially no conductance of the electrical signals along the surface direction of the film from areas surrounding the electrode, and by applying the electrode to the skin via the thin film. Electrical signals can be detected from the skin or transmitted to the skin via the electrode and thin film. This method allows easy application of a liquid contact medium for an electrode without worrying about interference between adjacent electrodes as previously occurred with gels, creams, or pastes. Because of these conductance characteristics of the thin film, electrical signals are detected only at the electrode site itself and spurious signals from areas adjacent to the electrode are filtered out. Thus, not only interference between adjacent electrodes, but also spurious signals from areas adjacent to the electrode are avoided. Accordingly, there is no need to be careful to apply the conductive liquid only at the electrode site as is necessary with gels, creams or pastes. Moreover, the conductive liquid can be made in a form so that little or no clean-up is required and so that they do not stain the patient's clothing. In addition, the method of the invention is very economical in view of the low cost of the conductive liquid and electrolyte that can be employed in the invention.

DETAILED DESCRIPTION OF THE INVENTION

The conductive liquid contact medium employed in the method of the present invention can be any liquid which will form a thin film on the skin of a patient which will conduct a predetermined electrical signal (e.g., an ECG electrical signal) through the thickness direction of the film, but which will not substantially conduct such an electrical signal along the surface direction of the thin film. In order to be conductive, the liquid will normally contain an electrolyte. Any liquid that is conductive itself or can be made conductive by use of an electrolyte can be employed in the method of the invention, but liquids that leave little or no residue or that are easily cleaned up are preferred. The conductive liquid should also be physiologically compatible with the patient's skin, i.e., it should not cause any adverse reactions on the skin. For example, suitable liquids include water, alcohol, acetone, dimethylsulfoxide (DMSO), dimethyl foramide (DMF), or other polar solvents. Water, alcohol and mixtures thereof are preferred.

As electrolyte, the conductive liquid can contain, any material that will ionize in the liquid to give the desired conductance. The electrolytes should likewise be physiologically compatible with the patient's skin. Example of suitable materials include ionizable salts, such as salts of strong acids and strong bases or of weak acids and weak bases; weak acids and/or weak bases, or buffer solutions thereof. For example, inorganic salt such as potassium chloride, sodium sulfate, or sodium chloride, and organic acids or salts such as citric acid, potassium citrate, and potassium acetate can be employed. Potassium chloride is a preferred electrolyte.

The conductive liquid used in the method of the invention preferable has a pH of about 5 to about 9 and more preferably of about 7. High and low pH values can have an adverse effect on the results obtained with the present method depending upon, for example, the electrode being employed, etc.

The conductive liquid used in the method of the present invention can also include oil solubilizing surfactants, including ionic and non-ionic surfactants. These surfactants solubilize the oil layer on the skin and penetrate the Keratin layer. They also lower skin resistance. Examples of suitable surfactants include sodium hexametaphosphate, trisodium phosphate and materials sold under the trademarks TWEEN and SPAN by Atlas Chemical. The surfactants can also serve as the electrolyte in the liquid, i.e., a separate electrolyte is not necessary where the surfactant has sufficient conductive characteristics by itself.

The conductive liquid employed in the method of the invention can also include various other additives such as perfumes, colorants, and preservatives. Since these materials are conventional in the art, they are not recited in detail here.

The conductive liquid can contain varying amounts of electrolyte, depending upon the thickness of the thin film to be employed, the electrical signals being measured, etc. The concentration of the electrolyte and the thickness of the film must be such that electrical signals will be conducted through the thickness direction of the film to an electrode attached to the skin, but such that there will be substantially no conductance of the electrical signals along the surface direction of the film, i.e., from areas adjacent to the electrode. Concentrations of from about 0.01 to about 15% by weight in water can be employed in the method of the invention. Typically, however, concentrations of from about 0.25 to about 4% by weight, and preferably from about 0.5 to about 2.5% by weight, of electrolyte are employed.

If the conductive liquid includes a surfactant which is also an electrolyte, the amount of surfactant is usually selected so that the total electrolyte concentration is within the above-discussed ranges. Generally, sufficient amount of surfactant is employed to reduce the skin resistance and therefore increase conduction of the desired electrical signals through the skin. Typically, from about 0.05 to about 2.0% by weight of surfactant can be employed in the conductive liquid.

The conductive liquid can be applied to the skin of the patient by any method which will produce a thin film within the required criteria. Examples of suitable methods include spraying, rolling, dabbing and brushing on the film to the skin of the patient. Spraying of the conductive liquid onto the skin of the patient preferred because of better hygiene, i.e., there is no need for the applicator to make contact with the skin of the patient. The apparatus for performing these methods of application are conventional in the art. For example, in spraying the conductive liquid onto the skin of a patient, any suitable aerosol or pump container can be employed, preferably one which atomizes the liquid upon spraying.

The conductive liquid is applied to the skin in a sufficient thinness or thickness so that electrical signals will be conducted through the thickness direction of the film to or from an electrode attached to the skin, but so that there will be substantially no conductance of the electrical signals along the surface direction of the thin film. The required thickness or thinness varies with the composition of the film, the solvent, electrolyte, etc. employed, and the strength of the electrical signal itself. If less electrolyte is used or the liquid is made less conductive by some other means, a thicker film can be employed. Typically, the conductive liquid is sprayed onto the skin of a patient so that the person making the application can see the "glistening" of the film, but not so much so that the liquid will run off the skin of the patient.

The method of the present invention can be used in any technique for measuring electrical signals to or from the skin of a patient, e.g., in measuring electrocardiograms (ECG), electroencephalogram (EEG), electromyogram (EMG), and biofeedback signals and the like. All that need be done is to apply the conductive film to the skin of the patient and then attach the desired electrode to the desired site via said film. There is no need to be concerned with interference between electrodes, so long as the electrodes are placed in a normal configuration, which always is sufficiently far apart on the skin so that there is substantially no conductance along the surface direction of the film between the electrodes. Of course, if desired a separate film for each electrode could be employed, but this extra precaution is not normally necessary.

The following examples are intended to illustrate, but not to limit, the present invention.

EXAMPLE 1

A conductive liquid comprising water containing 1% by weight of potassium chloride and 1% by weight of soduim hexametaphosphate was prepared. This solution was placed in a clean ordinary spray container having an atomizing spray pump, such as a hair spray container.

The prepared conductive liquid was sprayed on each area to which an ECG electrode was to be applied. Care was taken not to let any of the sprayed areas for the electrodes overlap. A sufficient amount of the solution was applied so that the person applying it could see the film but not so much that the conductive liquid ran off the skin of the patient. The ECG electrodes were then applied to each separate sprayed area and readings were taken. ECG readings were obtained which were as good as with conventional gels or pastes.

EXAMPLE 2

The conductive liquid of Example 1 was applied to the skin of a patient by spraying the entire area where a number of ECG electrodes were to be applied, without any regard to placement of the electrodes, i.e., the sprayed ares for adjacent electrodes thus overlapped.

The results obtained by the method of this example were the same as in Example 1 above where no overlap between electrode sites occurred. Thus, the method of the present invention surprisingly provides good electrical contact between the skin of the patient and an ECG electrode, without the need to be concerned with interference between the electrodes because of conduction along the surface direction of the contact medium as with gels and/or paste. Because only small amounts of potassium chloride and sodium hexametaphosphate are employed, no clean up is required, and there is no possibility of staining the patient's clothing as can occur with conventional gels or pastes. Moreover, the method of this example is much more economical than use of gels or pastes.

EXAMPLE 3

The procedure of Example 2 was repeated, except that the conductive liquid was water containing 1% by weight sodium chloride and 1% by weight sodium hexametaphosphate. The results obtained by this method provided good ECG readings, but sodium chloride, as expected, was less conductive than potassium chloride.

EXAMPLE 4

The procedure of Example 2 was again repeated, except that 1% by weight trisodium phosphate was employed in place of the sodium hexametaphosphate. This method provided fairly good ECG readings, but the pH was somewhat higher because of the trisodium phosphate and some drifting of the signal was obtained.

EXAMPLE 5

The procedure of Example 2 was again repeated, except that the conductive liquid contained 1% by weight citric acid in place of the potassium chloride. This method provided good ECG readings, but citric acid was less conductive than the potassium chloride.

EXAMPLE 6

The procedure of Example 2 was repeated, except that 1% by weight of potassium citrate was used in place of the potassium chloride. This method again provided good ECG readings.

EXAMPLE 7

The procedure of Example 2 was repeated, except that 1% by weight of potassium acetate was used in place of the potassium chloride. Again, this method provided good ECG readings.

EXAMPLE 8

A conductive liquid was prepared by dissolving 12% by weight potassium citrate and 1% by weight sodium hexametaphosphate in water. This conductive liquid was employed in the method described in Example 2 above. This method provided fairly good ECG readings, but the results were not as good as with some of the lower concentrations of electrolytes and it leaves a slight residue.

It will be understood that the embodiments described herein are merely exemplary and that a person skilled in the art may make many variations modifications without departing from the spirit and scope of the invention. All such modifications and variations are intended to be included within the scope of the invention as defined in the appended claims.

What is claimed is:

1. A method for applying a plurality of electrodes to the skin of a patient, said method comprising the steps of applying a thin film of a physiologically compatible conductive liquid to the skin of said patient, said film being of sufficient thinness so that electrical signals will be conducted through the thickness direction of said film to an electrode attached to said skin but so that there will be substantially no conductance of said electrical signals along the surface direction of said film; and applying a plurality of electrodes to said skin via said thin film at a sufficient distance from one another so that there is substantially no conductance between said electrodes through said film.

2. A method according to claim 1, wherein said conductive liquid comprises an electrolyte and a member selected from the group consisting of water, alcohol, acetone, dimethylsulfoxide, dimethyl formamide, and mixtures thereof.

3. A method according to claim 1, wherein said conductive liquid comprises water and electrolyte.

4. A method according to claim 2 or 3, wherein said conductive liquid comprises from about 0.1 to about 15% by weight of said electrolyte.

5. A method according to claim 2 or 3, wherein said electrolyte is selected from the group consisting of potassium chloride, sodium chloride, sodium sulfate, salts of organic acids, oil solubilizing surfactants and mixtures thereof.

6. A method according to claim 1, wherein said conductive liquid comprises an oil solubilizing surfactant.

7. A method according to claim 6, wherein said oil solubilizing surfactant is sodium hexameta phosphate.

8. A method for detecting electrical signals from or transmitting electrical signals to the skin of a patient, said method comprising the steps of applying a thin film of physiologically compatible conductive liquid to the skin of a patient, said film being of sufficient thinness so that electrical signals can be conducted through the thickness direction of said film to or from an electrode attached to said skin but so that there will be substantially no conductance of said electrical signals along the surface direction of said film; applying a plurality of electrodes to said skin via said thin film at a sufficient distance from one another so that there is substantially no conductance of said electrical signals between said electrodes through said film; and detecting or transmitting said electrical signals through said thin film with said electrodes.

9. A method according claim 8, wherein said electrodes are ECG electrodes and heart signals are being detected.

10. A method according to claim 8 or 9, wherein said conductive liquid comprises an electrolyte and a member selected from the group consisting of water, alcohol, acetone, dimethylsulfoxide, dimethyl foramide, and mixtures thereof.

11. A method according to claim 8 or 9, wherein said conductive liquid comprises water and electrolyte.

12. A method according to claim 11, wherein said conductive liquid comprises from about 0.1 to about 15% by weight of said electrolyte.

13. A method according to claim 11, wherein said electrolyte is selected from the group consisting of potassium chloride, sodium chloride, sodium sulfate salts of organic acids, oil solubilizing surfactants and mixtures thereof.

14. A method according to claim 8, wherein said conductive liquid comprises an oil solubilizing surfactant.

15. A method according to claim 14, wherein said oil solubilizing surfactant is sodium hexameta phosphate.

* * * * *

REEXAMINATION CERTIFICATE (1649th)

United States Patent [19]

Buchalter

[11] B1 4,465,074

[45] Certificate Issued Mar. 3, 1992

[54] METHOD OF APPLYING AN ELECTRODE TO THE SKIN OF A PATIENT

[75] Inventor: Gilbert Buchalter, Milburn, N.J.

[73] Assignee: Milburn Marketing Associates, Millburn, N.J.

Reexamination Request:
No. 90/002,324, Apr. 19, 1991

Reexamination Certificate for:
Patent No.: 4,465,074
Issued: Aug. 14, 1984
Appl. No.: 370,278
Filed: Apr. 20, 1982

[51] Int. Cl.$^5$ .................................... A61B 5/0402
[52] U.S. Cl. ................................ 128/639; 128/803
[58] Field of Search ........................... 128/639–641, 128/802, 803

[56] References Cited

U.S. PATENT DOCUMENTS

3,567,657  3/1971  Lichtenstein .

FOREIGN PATENT DOCUMENTS

911185  11/1962  United Kingdom .

OTHER PUBLICATIONS

Littmann, "Electrode Contact Fluid in Electrocardiography", 4 Am. J. of Cardiology p. 554 (1959).
Hartridge, "Methods of Reducing the Errors in Electrical Testing Due to Variations in Skin Resistance", IV Brit J. of Radiology pp. 652–657 (1931).
Neiss Instruction Manual for Applicard TE System (1975) (and translation).
Applifluid Trademark Application (1975) (and translation).
Applifluid Brochure (undated) (and translation).
Lewes, "Electrode Jelly in Electrocardiography", Brit. Heart J., 27:105 (1965).
Geddes, Electrodes and the Measurement of Bioelectric Events, Chapter 2, "Surface Electrodes", pp. 44–60 (John Wiley & Sons, Inc. 1972).
Geddes and Baker, Principles of Applied Biomedical Instrumentation, Chapter 9–8, "Electrode Electrytes", pp. 234–238 (John Wiley & Sons, Inc. 1975).
"EKG sol—the original electrode cream", advertising brochure of Burton, Parsons & Co., Inc. (Jun. 1975).
Deposition Transcript of Mary Tompkins taken on Jan. 26, 1989 for Millburn Marketing Associates v. Parker Laboratories, Inc., Docket No. 88-575, Eastern District of New Jersey, pp. 1, 4–6 and 98–104.
Declaration of Marvin Moskowitz dated Jan. 13, 1989, Millburn Marketing Associates v. Parker Laboratories, Inc. Docket No. 88-575, Eastern District of New Jersey.
The Condensed Chemical Dictionary, p. 944 (G. Hawley, rev., 10th ed. 1981).

*Primary Examiner*—Lee S. Cohen

[57] ABSTRACT

A method is disclosed for applying electrode to the skin of a patient in which a thin film of a conductive liquid is applied to the skin of the patient. The thin film is of sufficient thinness so that electrical signals will be conducted through the thickness direction of the film to or from an electrode attached to the skin but so that there will be substantially no conductance of the electrical signals along the surface direction of the film to or from adjacent areas surrounding the electrode. The electrode is then applied to the skin of the patient via the thin film. Electrical signals can be detected from the patient or transmitted to the patient via the electrode and conductive thin film, e.g., ECG signals.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-15 is confirmed.

* * * * *